United States Patent [19]
Vilkomerson et al.

[11] Patent Number: 5,161,536
[45] Date of Patent: Nov. 10, 1992

[54] ULTRASONIC POSITION INDICATING APPARATUS AND METHODS

[75] Inventors: David Vilkomerson, Princeton; David Lyons, Trenton, both of N.J.

[73] Assignee: Catheter Technology, North Brunswick, N.J.

[21] Appl. No.: 673,949

[22] Filed: Mar. 22, 1991

[51] Int. Cl.$^5$ .............................................. A61B 8/00
[52] U.S. Cl. ............................ 128/660.07; 128/662.05
[58] Field of Search ...................... 128/660.07, 660.04, 128/660.10, 660.01, 662.05, 754, 662.03

[56] References Cited

U.S. PATENT DOCUMENTS

| | | | |
|---|---|---|---|
| 4,236,221 | 11/1980 | Cribbs et al. | 128/660.01 |
| 4,249,539 | 2/1981 | Vilkomerson et al. | 128/754 |
| 4,407,294 | 10/1983 | Vilkomerson | 128/662.05 |
| 4,508,122 | 4/1985 | Gardineer et al. | 128/660.10 |
| 4,697,595 | 10/1987 | Breyer et al. | 128/662.06 |
| 5,040,225 | 8/1991 | Gouge | 128/660.04 |
| 5,076,278 | 12/1991 | Vilkomerson et al. | 128/662.03 |

Primary Examiner—Kyle L. Howell
Assistant Examiner—George Manuel
Attorney, Agent, or Firm—Arthur L. Plevy

[57] ABSTRACT

An ultrasonic imaging system employs a processing circuit which enables the imaging system to accurately display the location of an element in a body by utilizing a transducer which provides an electric signal when an ultrasonic wave impinges thereon. The electric signal is processed to determine the maximum amplitude signals during an entire frame of the ultrasonic imaging system. The signals are characterized in terms of the line at which the signal appears or the ray at which the signal appears and the pixel or location along that line. This information regarding ray and pixel serves as X-Y coordinates enabling one to accurately locate the element and transducer on the displayed image by intensifying the display at that location or by adding color or by producing some other visual effect such as blinking, and so on. Thus the disclosed apparatus in its various forms provides ultrasonic position indication without adjustment whereby one shows the exact location of the localizing transducer.

30 Claims, 10 Drawing Sheets

FIG-6
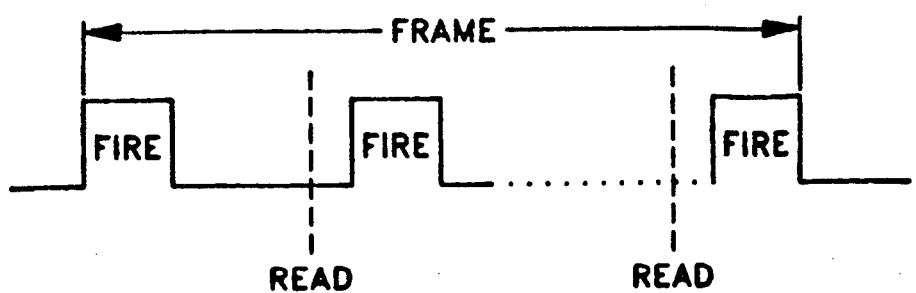
FIG-7
| | FIRE # (RAY) | | | | | | | | | |
|---|---|---|---|---|---|---|---|---|---|---|
| | 0 | 1 | 2 | 3 | 4 | 5 | 6 | 7 | 8 | ......N |
| AMP | 6 | 9 | 10 | 3 | 30 | 33 | 38 | 34 | 35 | |
| PIXEL Y (COO) | 13 | 27 | 41 | 52 | 22 | 23 | 24 | 25 | 28 | |
FIG-8A
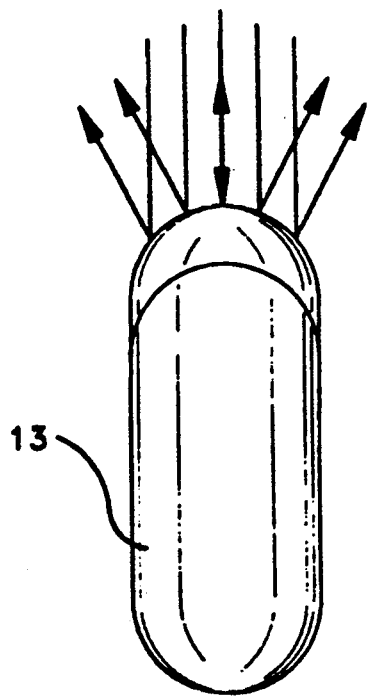
FIG-8B
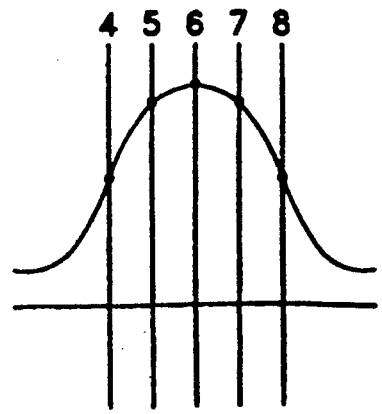

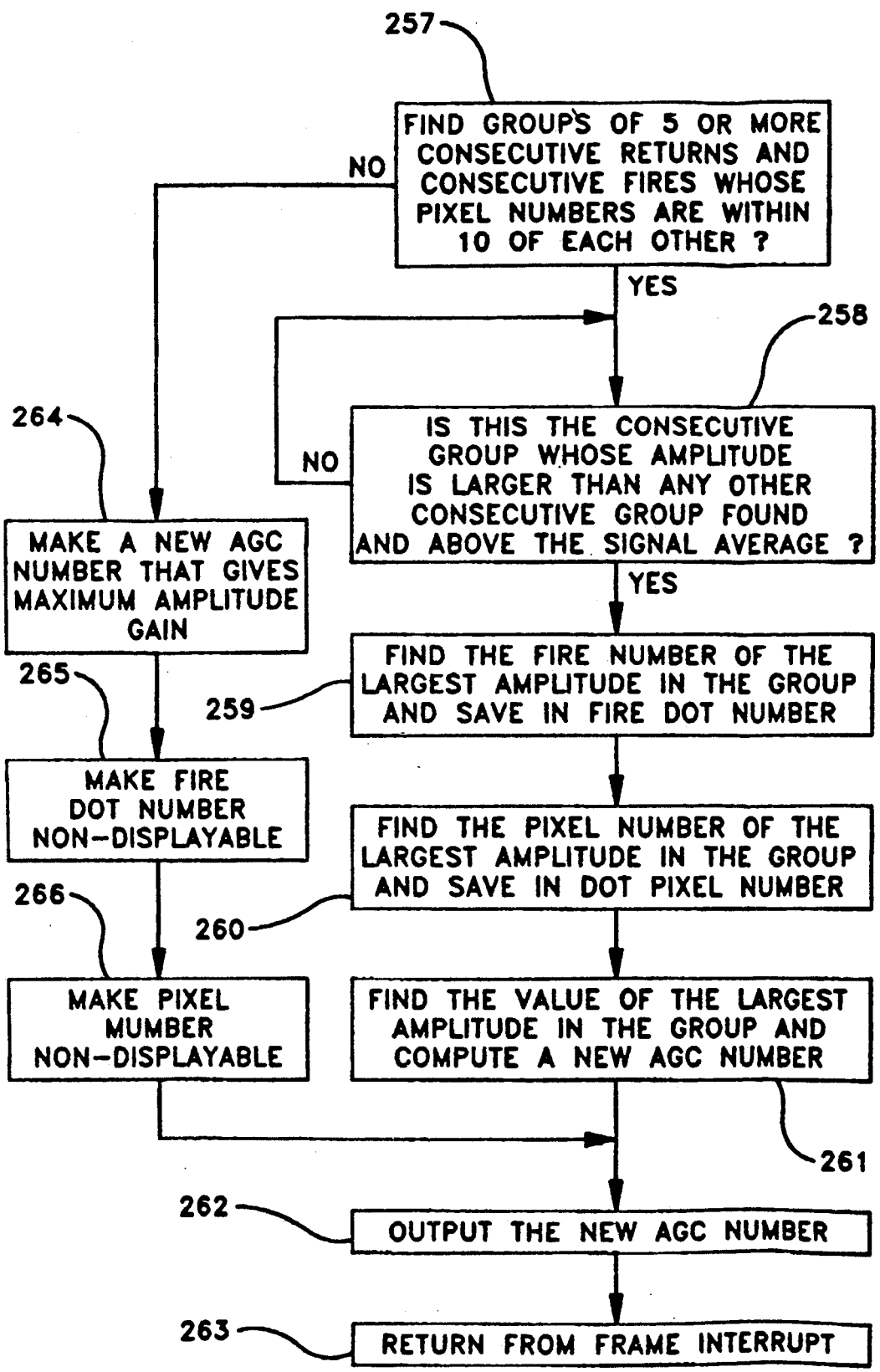

ULTRASONIC POSITION INDICATING APPARATUS AND METHODS

This invention relates to ultrasonic imaging systems and more particularly to the use of an ultrasound system for locating the position of an object within a body, for example a medical device, such as a catheter, within a living body.

BACKGROUND OF THE INVENTION

The accurate placement of catheters and other medical devices has become important in recent years for the treatment of a variety of illnesses, for example, the balloon angioplasty of coronary and peripheral arteries. There are many new uses that will increase the need for precise catheter placement which include stricture dilation performed in the prostrate, selective infusion of drugs to specific sites, and a host of other applications. Catheter placement has been done almost exclusively under x-ray guidance. In such techniques the contrast medium is sent through the catheter while it is being observed by x-ray fluoroscopy, the contrast moving through the catheter and the jet at the tip showing the location. The physician frequently a "interventional radiologist" guides the catheter between x-ray sightings. Limitations on catheter placement by x-rays include the safety issues based on x-ray dosage which were received by the patient and physician and the contrast medium load on the patient's kidneys. Other limitations are related to the need for the procedure to take place in a special room and the need for a radiologist to also be in attendance during the procedure. As one can ascertain both of these requirements add inconvenience and expense to the procedure. Ultrasonic imaging can provide excellent images of many of the blood vessels and prostatic urethra in which these procedures take place. In addition to visualizing the vessels, the Doppler capability of ultrasonic imaging allows measurements of flows achieved by the catheter, as to whether to augment flow or diminish it. There has not been any reliable method of localizing a catheter's position by ultrasonic imaging. This is because the ultrasonic image of the catheter depends on the angle of the catheter to the ultrasonic beam as the catheter moves in the vessel. Some portion of it may become visible, but which portion and when it becomes visible depends on the exact path of the vessel imaged and the particular location of a isonifying ultrasonic source. For these reasons no one uses ultrasound to try to accurately place a balloon catheter, for example, within a peripheral artery even though the artery and the blockage are visible by ultrasonic imaging. The prior art was cognizant of the use of ultrasound imaging to locate the tip of a needle.

Reference is made to U.S. Pat. No. 4,249,539 issued on Feb. 10, 1981 to David H. R. Vilkomerson et al and entitled ULTRASOUND NEEDLE TIP LOCALIZATION SYSTEM. This patent describes a means for localizing a needle tip using an ultrasound imaging system. The apparatus consists of a small transducer whose location was to be determined, receiving the transmitted pulse of an ultrasonic imaging system and sending it back to the imaging system to show its location. In particular, the patent described the method whereby the return signal was generated electronically and returned directly to the imaging system rather than acoustically back through the body. More general uses of this technique, for example, locating interventional devices in an artery by means of catheter carried transducers are being contemplated. Such uses require an accurate method of showing the position of the localizing transducer. The technique described had various associated problems. In the method described in the patent, a comparator was employed to measure the received signal compared to a reference level. When the received signal was higher the apparatus would generate a pulse that would, after being delayed a time equal to that used in propagating from the ultrasound system to the transducer (i.e., simulating the time required of a pulse reflected by the localizing transducer if direct reflection were used), be inserted into the signal stream of the ultrasonic imaging system, causing a "dot" to appear at the location of the transducer. A problem with that method is that the reference level must be constantly re-adjusted for varying signal levels. When the transmitting transducer is close to the localizing transducer, not only the main lobe but the side lobes of the imaging beam will exceed the reference level, causing a "dot" to appear in several beam positions of the image resulting in a smear in the image.

If the reference level is reduced to obtain the single beam position that represents the center of the imaging beam and which produces the most accurate location of the localizing transducer, a slight change in the position may reduce the signal level at the localizing transducer enough to eliminate any signal whatsoever, thus erasing the "dot". Thus the prior art required a need for continuous readjustment of the reference level to achieve localization and is a serious drawback to system operation. Also in regard to this particular technique, see an article entitled ULTRASONICALLY MARKED CATHETER—A METHOD FOR POSITIVE ECHOGRAPHIC CATHETER POSITION IDENTIFICATION by B. Breyer, et al and published in The Medical and Biological Engineering and Computing Journal, May 1984, Pages 268-271. As one will understand from that article, the system described has the above-noted disadvantages.

It is therefore an object of the present invention to provide apparatus to be employed with an ultrasound system which eliminates the need for readjustment of any kind while achieving the optimum localization of the receiving transducer position.

A further object of the present invention is to provide an accurate and improved system for determining the position of an ultrasonic transducer.

SUMMARY OF THE INVENTION

An apparatus for responding to a transducer within an area of a body, said transducer of the type which responds to ultrasonic energy impinging on a surface thereof by returning a signal, comprising an ultrasound imaging system for imaging the area of the body to cause said transducer to return a signal each time ultrasonic energy impinges thereon, said system including means for providing a display of said area by converting imaging information into a given number of scan lines to cover said imaged area with said given number of scan lines indicative of a frame, and means responsive to said returned signals during said frame to analyze said signals on a frame to frame basis for providing a control signal enabling said means to optimally respond to said returned signals.

BRIEF DESCRIPTION OF THE FIGURES

FIG. 6 is a timing waveform diagram showing fire pulses employed in this invention.

FIG. 7 is a format depicting the layout of the memory array useful in this invention.

FIGS. 8A and 8B are diagrams depicting the operation of a transducer having ultrasonic waves impinging thereon.

FIG. 12 is a flow chart useful in describing the operation of the frame interrupt mode.

DETAILED DESCRIPTION OF THE FIGURES

Figure 1:
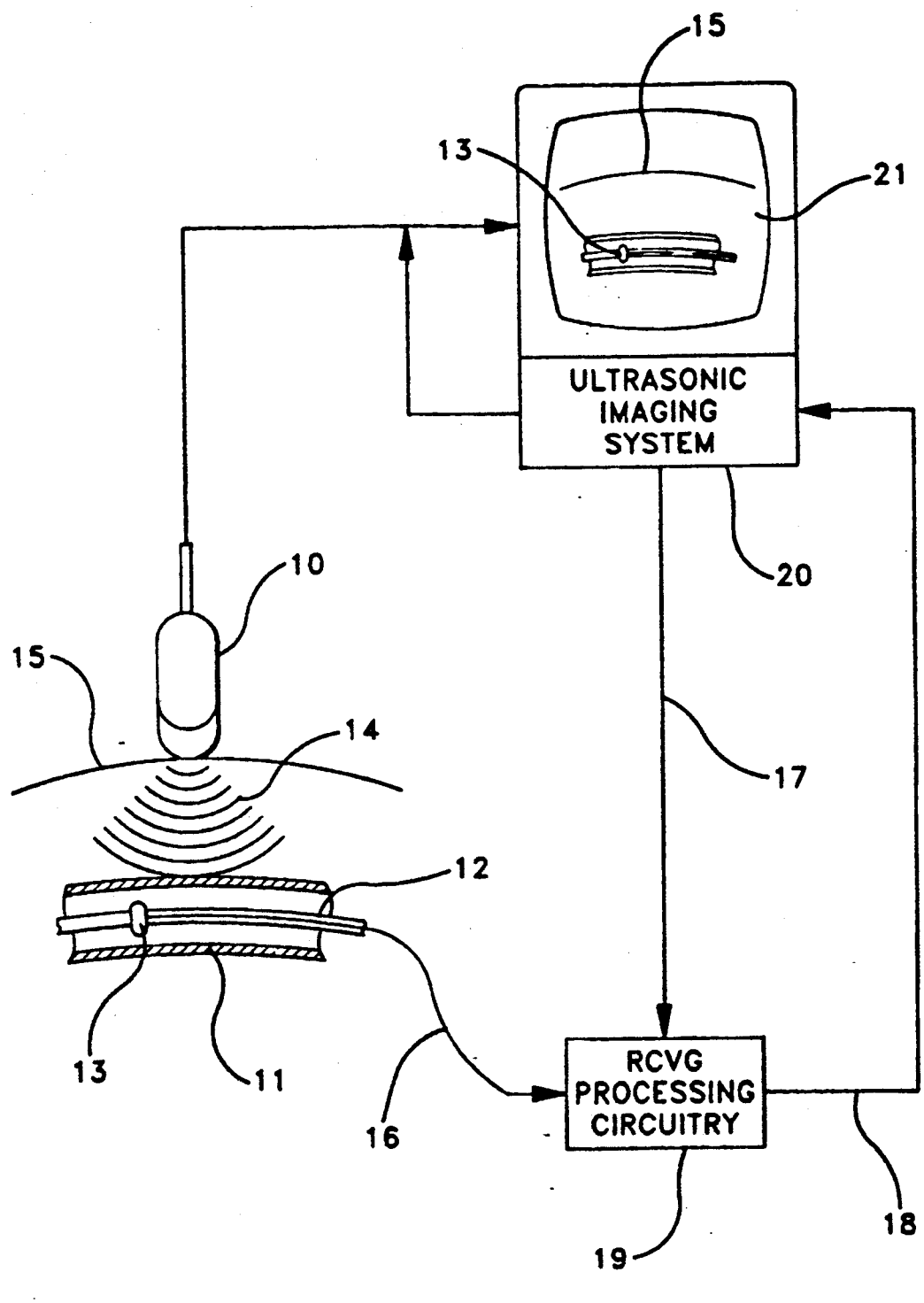
FIG. 1 is a block diagram showing an ultrasonic imaging system incorporating processing circuitry according to this invention.

Referring to FIG. 1 there is shown a simple block diagram of an ultrasonic imaging system employing the present invention. The ultrasonic imaging system includes a display 21, which enables the practitioner or user of the system to visualize the portion of a patient's body that is being scanned. Ultrasonic imaging systems have been widely used in medical applications because such systems enable imaging of internal structures of the body without the use of harmful forms of radiation. As seen, the ultrasonic imaging system 20 is associated with a scanning head 10. The scanning head 10 is a hand held unit which the physician manually moves about the body of a patient to thereby perform imaging according to a particular ailment or complaint. As is known in the prior art, it is desirable for hand held scanners as 10 utilizing ultrasound to provide a clear scan picture of the volume of tissue under investigation. The scan picture or display as indicated previously is presented on a display 21. As shown in FIG. 1 the hand held scanner 10 provides a beam of ultrasonic waves 14 which beam is directed into the body 15 of a typical patient under investigation. As indicated, it is a desire to utilize ultrasound to trace the progress of a catheter which may be inserted into an artery, vein, or other body part of a patient under investigation. Such catheters are widely employed. As seen in the figure, a catheter 12 is inserted into an artery 11 of a patient and is moved by a practitioner. As seen, the display 21 depicts the artery as well as the catheter in a conventional manner. In order to locate the catheter so that the physician in viewing the display 21 is able to determine the progress of the catheter, there is shown a transducer 13 which is secured to the catheter and is capable of providing an electrical signal when the surface of the transducer is impinged upon by ultrasonic waves. In this manner the electrical signal provided by the transducer 13 is directed via a wire 16 to the input of a receiving processing circuitry module 19. The circuitry module 19 as shown interfaces with the ultrasonic imaging system via input cable 18 and the ultrasonic imaging system interfaces with the receiving processing circuitry via a cable 17. It is further indicated that the coupling can be done by many different techniques such as electromagnetic or electrostatic coupling. In this manner one can actually couple to, for example, the leads emanating from the scan head 10 to the ultrasonic imaging system without actually making a direct connection to the lead but can do so by means of electromagnetic couplers, and so on. Coupling can also be acoustic by transponding via transducer 13. As will be further explained, it is an objective of the present invention to enable a physician to accurately perceive the location of the catheter 12 in regard to the front of the catheter on the display. Accordingly the system determines the position of the transducer 13 which is located at a predetermined position on the catheter. In this manner, the receiving processing circuitry 19, as will be explained, provides signals to the ultrasonic imaging system which determine the exact location of the catheter and cause the display to display that location so the physician knows exactly where the catheter is being moved and knows the position of the catheter. The transducer 13, for example, may be the type of transducer described in a co-pending patent application entitled ANNULAR ULTRASONIC TRANSDUCERS EMPLOYING CURVED SURFACES USEFUL IN CATHETER LOCALIZATION filed on Oct. 15, 1990 as Ser. No. 597,508 and assigned to the assignee herein. Before describing the particular system according to this invention, a brief description of the operation will be given in conjunction with the block diagram of FIG. 1.

As indicated, the hand held scanner 10 emits ultrasonic waves 14 which essentially impinge upon the transducer 13 causing the transducer 13 to produce an electrical signal. This signal is transmitted along wire 16 where it is received by the receiving processing circuitry 19. The receiving processing circuitry 19 is capable of determining the exact position of the transducer and therefore the catheter in regard to the image being displayed by the imaging system 20. Thus the receiving processing circuit then produces an electrical signal which is directed to the ultrasonic imaging system causing the location of the transducer 13 to be clearly indicated on the display. This can occur by increasing the intensity of the display at that location or by providing a symbol, or by causing the display to flash on and off or by numerous other techniques including adding a different color to the display to indicate the location of the transducer. In this manner by knowing the location of the transducer with respect to the catheter as, for example, so many inches from the tip of the catheter or in the center of the catheter, the physician immediately knows the location of the catheter by viewing the display. For a general understanding of ultrasonic imaging devices including a particular hand held scanner, reference is made to U.S. Pat. No. 4,508,122 entitled ULTRASONIC SCANNING APPARATUS AND TECHNIQUES issued on Apr. 2, 1985 to B. Gardineer, et al and assigned to Ultramed, Inc. of New Jersey. As will be explained, the present invention provides a presentation of the location of the transducer associated with the catheter that enables the system to evaluate the received signal over the entire image frame so that the most accurate localizing image is retrieved and introduced into the actual display. In this manner there is no need for readjustment of any kind to achieve the optimal localization of the receiving transducer position and none of the problems evidenced by the prior art exist in the system according to the present invention.

Figure 2:
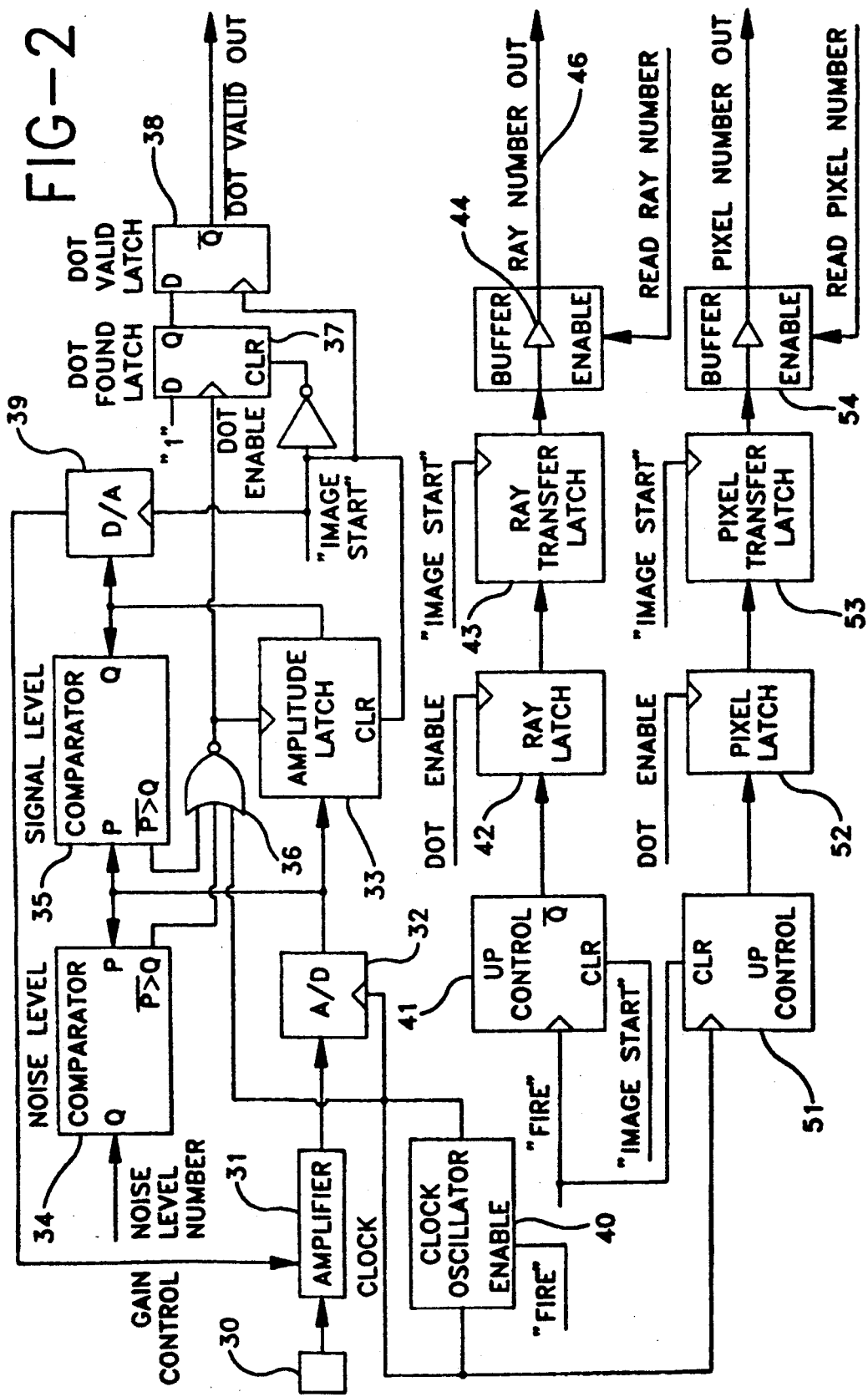
FIG. 2 is a detailed block diagram of an ultrasonic position indicating apparatus according to one embodiment of this invention.

Referring to FIG. 2 there is shown a block diagram of a catheter locating system in accordance with this invention. In FIG. 2 the catheter locating system will operate with an ultrasound system which essentially allows the circuit to interface with the existing scan converter included in such a system. Most ultrasound systems employ scan converting apparatus which essentially enables one to generate a proper display. In ultrasound systems the returning echos from the transmitted pulse provide one line of an ultrasonic image. That line in the ultrasonic image corresponds to the sequence of interfaces encountered by the sonic pulse as it propagates downwardly into the body of the patient. The term scan converter includes any scan controlled system to enable one to format a video display by controlling the scan of the display from such lines. Hence the term scan controller is a broader concept than scan converter. The line information is typically stored in a scan converter that assembles the information from the sequence of lines produced as the scanning head is moved along the body of the patient. The assembled image or frame is in a video format so that it can be displayed directly on a T.V. monitor or recorded on a video recorder, and so on. In such systems the length of the image line or how far down the instrument collects the echo information is set by how long the system receives echo returns. Thus the scan converter must accurately assemble the lines into an image. The determining factor in the accuracy and stability of the image is the positioning of the scan lines, and so on. Thus in FIG. 1, the image shown on display 21 consists of a predetermined number of lines whereby the predetermined number of lines constitutes a frame. This frame is typical in video parlance and essentially determines a discrete number of lines which are implemented by the scan converter. Essentially the start of the frame is the start of the image and is, for example, determined by the scan converter by means of a signal called "Image Start". This is a conventional signal and is shown in FIG. 2 as such. The "Image Start" signal as indicated is produced by all ultrasound systems employing scan converters and basically determines the start of the image. In a similar manner, the end of the image or the end of the frame is also determined by a pulse which, for example, can be the same exact image start pulse, as the start of a new frame is indicative of the end of the old frame. Between the "Image Start" pulses or frame pulses there are what is known in the art as FIRE pulses. Each FIRE pulse is a pulse which is being transmitted by the scanning head 10 and as indicated is indicative of one line of video information. Thus between each "Image Start" or frame pulse there are a plurality of FIRE pulses which determine, for example, the total number of lines which comprise the picture 21. As one can immediately ascertain, in order to determine the location of the transducer 13, one would therefore have to know the line that the transducer appears at in the video picture as well as the location of the transducer on that line as to whether it is in the center or towards the right or towards the left. Thus as indicated in the video art, one would have to know the coordinates of the transducer 13, at the X-Y address defining the location of the catheter or the X and Y addresses in the video display to define that location. Thus the position of the catheter on a line or on a ray (each pulse indicates a transmitted ray from the ultrasound system) and the exact position on that line or ray (pixel) is generated by this system to determine the location of the catheter in regard to the displayed image. Thus the circuit of FIG. 2 operates to do so, as will be explained. Referring to FIG. 2, reference numeral 30 depicts the transducer as, for example, 13 of FIG. 1 which as indicated when impinged upon by an ultrasound signal emanating from the scanning head will produce an electrical signal. Thus the electrical signal from the transducer 30 is coupled to the input of an amplifier 31. The output of the amplifier 31 is coupled to the input of an analog to digital (A/D) converter 32. The analog to digital converter 32 is of conventional design and may, for example, be an 8 bit or 16 bit analog to digital converter. The A/D converter 32 has one output coupled to the input of an amplitude latch circuit 33. The purpose of the amplitude latch circuit as will be explained is to store the largest amplitude emanating from the analog to digital converter 32 during a frame. The output of the A/D converter 32 is also directed to the P inputs of comparators 34 and 35. Each comparator 34 and 35 is a conventional digital comparator which can operate to compare a signal at the P input with a signal at the Q input and provide an output when the signal at the P input exceeds or is equal to the signal at the Q input. The operation of such comparators is well known. The output from the analog to digital converter 32 which is a digital output is applied to the P inputs of comparator 34 and comparator 35. The Q input of comparator 34 is derived from a noise level number which essentially is a digital number indicative of a predetermined threshold above which the system will operate. In order to compensate for noise which is produced in any such ultrasonic system there must be a certain threshold level that has to be exceeded before the system will operate. Thus the noise level number is a digital number which may be experimentally or empirically selected and applied to the Q input of comparator 34. Hence when the output signal from the analog to digital converter 32 at input terminal P exceeds the noise level number at input terminal Q, the comparator 34 produces an output which is directed to one input of NOR gate 36. NOR gate 36 enables the amplitude latch 33 which amplitude latch 33 will then store the output signal from the analog to digital converter 32. The P input of the comparator 35 is also coupled to the output of the analog to digital converter 32. The Q input of the comparator 35 is coupled to the output of the amplitude latch 33. In this manner the comparator 35 will operate when the signal from the A/D converter 32 is greater than the signal stored in the amplitude latch 33. The amplitude latch 33 always has stored therein the level of the signal which exceeds the previously stored signal and also which exceeds the noise level number. It is further seen that the gate 36 is enabled during the FIRE pulse. Thus during the FIRE pulse a clock oscillator 40 enables gate 36 to thereby assure that if either of the comparators 34 or 35 operate, that the amplitude latch will store the output from the analog to digital converter 32 in proper digital form. The output of the amplitude latch as indicated and shown also goes to a digital to analog converter 39 which converts the digital signal into an analog signal, which analog signal is used to control the gain of amplifier 31, amplifier gain control "AGC". The digital to analog converter 39 is latched at the "Image Start" to change the AGC signal, if necessary, each frame. Thus AGC is updated once per frame. Thus the gain of amplifier 31 is controlled as a function of the signal stored in the amplitude latch 33. When NOR gate 36 is operated, this provides the dot enable signal. The dot enable signal essentially is the signal which indicates to the system that the location of the transducer has been found. The dot enable signal now activates the dot found latch or flip-flop 37. The dot found latch is a normal DQ flip-flop which is always cleared at the "Image Start" pulse. It is of course understood that the amplitude latch is also reset at the "Image Start" pulse. Thus when the dot enable signal is provided the flip-flop 37 activates the dot valid latch 38 which again is another DQ flip-flop. As one can ascertain at the presence of the "Image Start" pulse, the dot valid output of flip-flop 38 will produce a high level indicating that a dot has been found during the last frame. The dot valid signal indicates that a symbol should appear in the image. The location of the dot is determined by circuitry which will be now described. The clock oscillator 40 as indicated can provide a single enable pulse during the firing condition but can also operate to control the analog to digital and digital to analog converters 32 and 39 as well as provide a clock for the up-down counters 41 and 51. As seen, up-down counter 41 is cleared at the "Image Start" pulse which means a clear at the beginning of the frame start. The input to up-counter 41 is the FIRE pulse. The FIRE pulse as indicated above occurs when the ultrasound system emits a pulse indicative of a single line of information. Thus the up-counter 41 counts this pulse. As seen during the generation of the dot enable signal via gate 36 the ray latch or line latch 42 is enabled. In this manner when the dot enable signal is provided, the contents of the up-counter 41 are stored in latch 42. This essentially determines the line in which the dot enable signal appeared. It is of course understood that as the amplitude varies or increases, the contents of the ray latch 42 will also change to always store the line associated with the dot enable signal. The output from the ray latch 42 is directed to latch 43 which is a ray transfer latch. The latch 43 is enabled by the "Image Start" signal. Hence at the end of a frame or the beginning of the next "Image Start" signal, the contents from the ray latch 42 are transferred and stored in the ray transfer latch 43. The output of the ray transfer latch 43 is coupled to the input of buffer 44 which essentially outputs the contents of the ray transfer latch 43 when commanded to do so by the Read Ray Number command present on the enable line of module 43. This Read Ray Number command is conventionally supplied by the scan converter of the ultrasonic imaging system being controlled. Thus the Ray Number Out appears on line 46 and is directed to the scan converter of the ultrasonic imaging system notifying the scan converter that the largest signal during the last frame appeared on a given line. The line has been defined and now the system must know where on the line the largest signal appeared. This coordinate is provided by means of up-counter 51. Up-counter 51 is cleared during each FIRE pulse and has its input coupled to the output of the clock circuit. Thus in this manner each line is broken up into a series of segments determined by the clock input to the up-counter 51. Thus during each FIRE pulse up-counter 51 counts during the length of the line. For example, a typical line may be broken up into many segments. During the dot enable the pixel latch 52 is enabled by means of the dot enable signal and hence the pixel latch stores the contents of the up-counter 51 during dot enable. The pixel transfer latch 53 operates in a similar manner to the ray transfer latch and is enabled by the "Image Start" signal whereby at the end of a frame, the contents from the pixel latch 52 are transferred to the pixel transfer latch 53. The buffer 54 outputs the pixel number to the scan converter of the ultrasonic imaging system when receiving the Read Pixel Number command. Hence in this manner the scan converter now receives the ray number out and the pixel number and therefore can now modulate that location by means of an increase in the intensity or by color or by pulsing the display on and off. In this manner one accurately determines the largest signal produced by the transducer 30 during the frame and marks that signal on the image for exactly locating the position of the catheter. It is of course understood that the largest signal may be indicative of the center position of the transducer 13. One knows the exact dimensions of the transducer 13 in regard to the overall display and hence one by using the ray number out and the pixel number out information can accurately provide a display of the transducer over more than one line or over more than one ray in the display to thereby give the practitioner an absolute clear view of the exact dimension of the transducer and the catheter with respect to the displayed image. It is, of course, understood that while the above-described system would produce the maximum output or the position of the maximum amplitude signal for a line and pixel it is of course understood that by a simple modification of the system shown in FIG. 2, one could provide a plurality of signals all of which are associated with large amplitude and then from such signals make a more accurate determination of the exact location of the catheter. For example, as one will ascertain the transducer 13 is essentially physically wider than one line of the image and may, for example, appear in four or five lines. The four or five lines all of which will have a large amplitude associated therewith, will also be approximately located at about the same pixel in consecutive lines. For example, the catheter may be as wide as lines 100, 101, 102, and 103 and being approximately at the same pixel or at close pixels during each line. Therefore, one would expect large signals during pixels for each of those lines. Thus it would become immediately apparent to one that the system can be accommodated to operate in this manner and store the four largest signals or a given number of large signals in consecutive lines at about the same pixel locations. When one indicates at about the same pixel location, one is essentially saying that the transducer may not be perfectly vertically oriented and may, in fact, be at a positive or negative slope with respect to the vertical or horizontal axis and therefore the pixel location associated with each of the lines may vary. As indicated above, the block diagram associated with FIG. 2 is pertinent when one has direct access to the scan converter of the ultrasonic imaging system. The reason for this is that the scan converter when receiving a ray and pixel number would know exactly where to insert the image of the catheter on the display. As explained above, the amplified signal from the localization transducer 30 is compared to the highest value previously experienced during the frame. The above discussion shows a digital implementation of the circuitry but as one can understand everything described above can be done in analog fashion as well, utilizing for example capacitor storage devices, and so on and hence one can operate directly with analog signals. It is, of course, understood that the digital implementation is more reliable in regard to noise and other variations. As indicated above, when a large amplitude is detected its position in both acoustic beam position representing the angle from the transmitting transducer and in time of occurrence representing the distance from the transmitting transducer is stored. Thus, at the end of the frame where one has completed the scan of the area of interest, the exact position of the highest signal is stored in the registers 43 and 53. The signal must be higher than the noise level for the system to be enabled. As indicated above, this information determines precisely the location of the dot in the image that represents the localizing transducer's position. In FIG. 2 the information is used to add the dot into the image by directly connecting to the scan converter whereby the beam number and time are translated to the proper position in the image. This localizing dot as displayed in the image can be shown in color by means of what is known as graphic overlay on the image. There can be multiple transducers which can be located and they can be coded differently, as one can ascertain.

Figure 3:
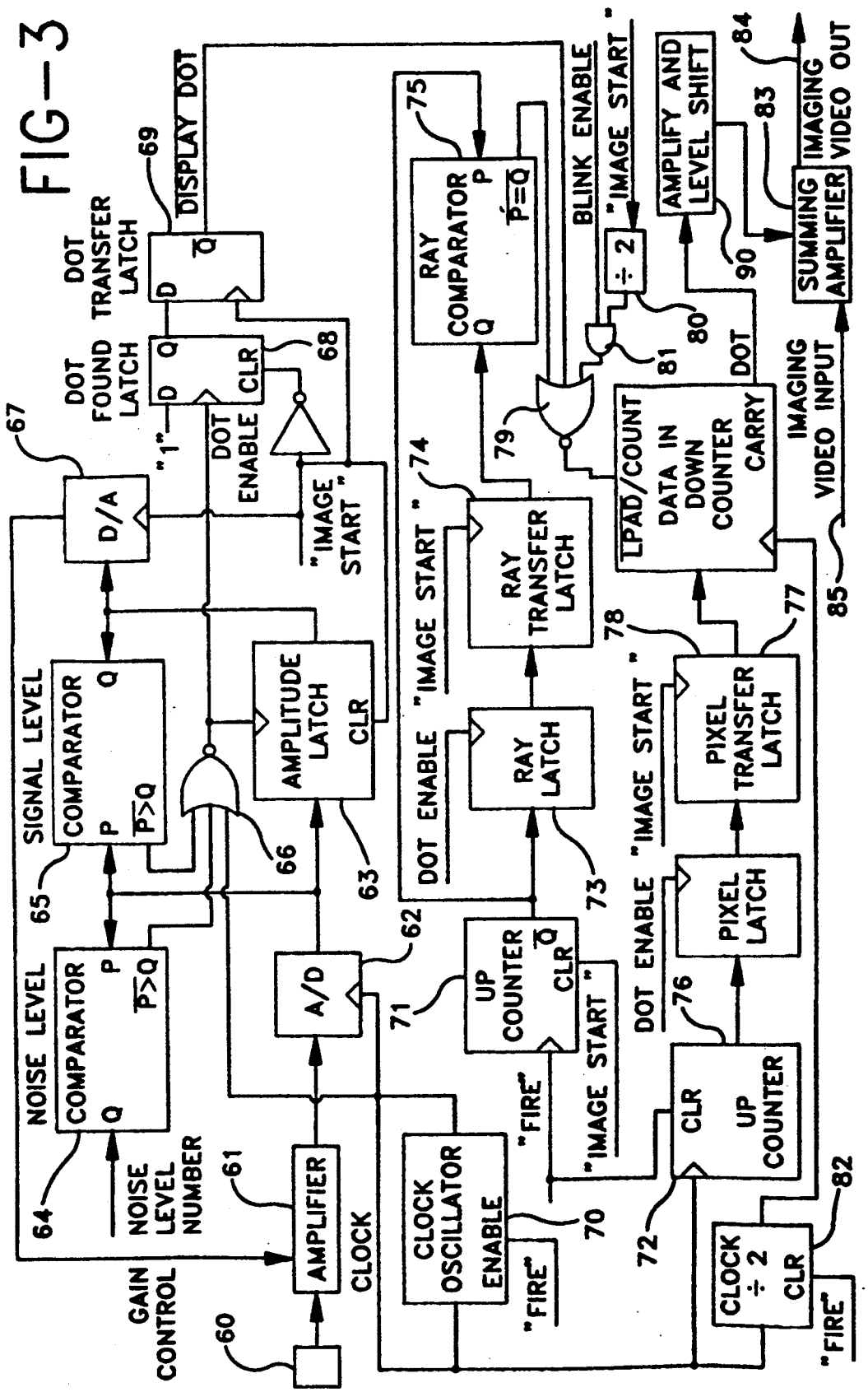
FIG. 3 is a detailed block diagram of an ultrasonic position indicating apparatus according to another embodiment of this invention.

Referring to FIG. 3 there is shown a technique which can be employed on ultrasonic imaging systems which do not have easy access to the scan converter. In the embodiment shown in FIG. 3 after the proper position is calculated, the dot is entered into the next frame. Thus the stored ray number where the signal was the highest is compared to the present ray number. When they are equal, a pulse is introduced into that transmitting transducer line at a time equal to twice the time measured between the transmit pulse and the maximum signal occurrence. The doubling in time compensates for the propagation time back from the localizing transducer to the transmitting transducer. Thus a bright dot is shown at the precise location of the localizing transducer. This doubling in time would not be required if transducer transponding is implemented as by pulsing the transducer. It is, of course, understood that the transducer 60 can be located on any medical device. As shown in FIG. 3 the catheter transducer 60 again is coupled to the input of the amplifier 61 whose output is supplied to A/D converter 62. The A/D converter 62 supplies inputs to the P input of comparator 64 and 65. Comparator 64 provides an output when the signal exceeds the noise level number input to comparator 64 which amplitude is stored in the amplitude latch 63. The comparator 65 again produces an output when the input signal from A/D converter 62 exceeds the amplitude value stored in latch 63. The digital to analog converter 67 controls the gain of amplifier 61. As noted, the digital to analog converter 67 is latched at "Image Start". Thus the AGC signal is updated once per frame. The output of NOR gate 66 again produces the enable signal which as indicated above operates the dot found latch at the "Image Start" or at the beginning or end of frame signal via the latch 68. The output of latch 68 is coupled to latch 69 which is the dot transfer latch. The display dot signal is now applied to the input of NOR gate 79 instead of to the scan converter. This will be further explained. In any event as indicated, the clock is applied to the analog to digital converter 62 and to the NOR gate 66 as well as to the up-counter 72 as previously indicated. However, the clock is also applied to a divide by two 82 which is cleared during the presence of each FIRE signal. This clock 82 is supplied to the Data In Down-counter 78 which will be described further to explain how the dot is provided in the system of FIG. 3. Similarly as described above, there is an up-counter 71 which up-counter 71 produces a count for each FIRE pulse occurring during the frame. The up-counter 71 is cleared by the "Image Start" signal. Thus the up-counter 71 counts each line in the image display. In a similar manner, the up-counter 72 is operated to provide a pixel count and is cleared upon each FIRE pulse and begins to count up, giving a predetermined number of pixels for each line or ray. Thus as seen, the pixel up-counter 72 operates in conjunction with the pixel latch 76 which is enabled by dot enable as well as the pixel transfer latch 77 which is enabled by the "Image Start" signal. The pixel information is applied to the data input of the down-counter 78. The output from up-counter 71 which has the line value stored therein is applied to one input of a ray comparator 75. The other input from the ray comparator 75 is applied from the ray transfer latch 74. In this manner the ray comparator 75 compares the present line number with the stored line number. Thus with the "Image Start" the ray latch value and the pixel latch value are transferred to the ray transfer latch 74 and the pixel transfer latch 77. Also the dot found latch value is transferred to the dot transfer latch 69 to generate the display dot signal. In the next image frame the ray comparator signals from comparator 75 provide a signal when the current image ray number is the same as the ray number stored in the ray transfer latch 74, which latches, at each "Image Start", the contents of ray latch 73. When this occurs, the value in the pixel transfer latch is loaded into the down-counter 78. The down-counter 78 is then decremented to zero with the clock 82 at one-half the frequency of that used to acquire the catheter location. This performs the necessary time doubling as described above. When the down-counter 78 reaches zero and produces the carry the resulting dot signal is amplified and level shifted via module 90. The output of module 90 which is the amplifier level shift is applied to the input of a summing amplifier 83. The summing amplifier receives at its input the imaging video input which is obtained from the ultrasonic imaging system. Thus the dot video information is summed with the imaging video information to produce an imaging video output signal on line 84. This imaging video output signal contains the dot location indicating the location of the catheter and is applied to the video signal of the display to thereby add the catheter location to that video signal. Also shown coupled to the input of NOR gate 79 is the output of AND gate 81 which receives a blink enable signal at one input and has at the other input an "Image Start" signal divided by 2 by means of divider 80. In this manner the gate 81 when enabled will enable the dot location to blink or to be provided every other frame which would provide a blinking action.

Figure 4:
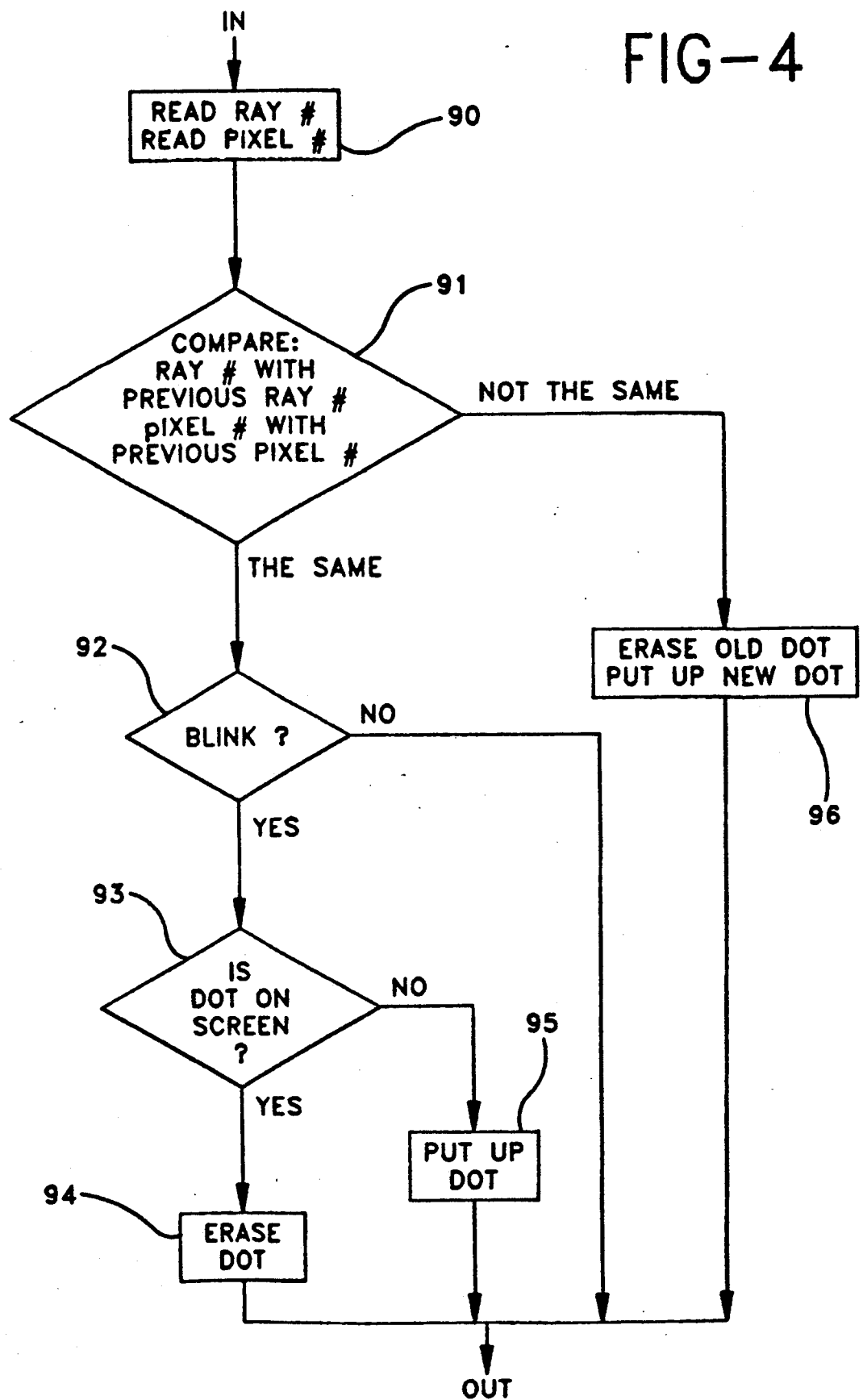
FIG. 4 is a flow chart useful in describing a mode of operation of another aspect of this invention.

Referring to FIG. 4 there is shown a flow diagram which can be implemented by hardware or via a microprocessor which further addresses the problem of adding the catheter location to an image display. As one will understand, ultrasonic imaging systems of the prior art utilize scan converters which may produce 4–20 frames a second. The catheter, for example, may be moved very rapidly or very slowly. If a catheter is moved slowly, then the transducer will be about the same position during a number of consecutive frames and as one will understand a dot is produced for each frame. Thus the number of dots produced is a function of the speed of movement. If the catheter is moved rapidly, then the dots will produce a line on the display instead of a pinpoint location of the catheter, as one will understand. In FIG. 4 there is shown a simple flow chart which can be implemented as indicated by conventional hardware or by a microprocessor as can, for example, the entire hardware shown in FIG. 2 and FIG. 3. In order to prevent a line representation or a smear on the display, the logic shown in FIG. 4 is used. As indicated, module 90 reads and stores the present ray and pixel number. The present ray and pixel number are compared with the previous ray and the previous pixel as indicated in module 91. If they are not the same, then as evidenced by module 96 the old dot location is erased or removed and a new dot is placed at the new pixel and ray location as indicated by module 96. If they are the same, then module 92 indicates as whether to provide a blinking of this location. If a blinking is not to be provided, then one leaves the program. If the blinking is to be provided then module 93 determines whether there is a dot on the screen. If there is a dot on the screen, the dot is erased as indicated by module 94. If there is not a dot on the screen, a dot is placed on the screen as indicated by module 95. In this manner one can now blink the dot every other frame as indicated by the flow chart. In a practical manner the flow chart indicated in FIG. 4 can be very simply implemented due to the fact that the value of each ray and each pixel during the generation of a dot are known plus the fact that the previous values of the ray and pixels are also stored by means of the latches. It should therefore be apparent to one skilled in the art that the above described techniques are extremely reliable in the fact that the system utilizes an entire image frame to determine the optimum signal during that frame and therefore provide the most accurate location information concerning the catheter in conjunction with the transducer coupled thereto. It is also apparent that many variations of the above can be utilized as, for example, more than one amplitude signal can be stored and compared to determine whether the transducer has appeared in consecutive lines which is normal procedure due to the finite size of the transducer. In this manner one can actually trace out the exact location of the transducer and therefore the catheter location during a display and on a frame-to-frame basis.

Figure 5:
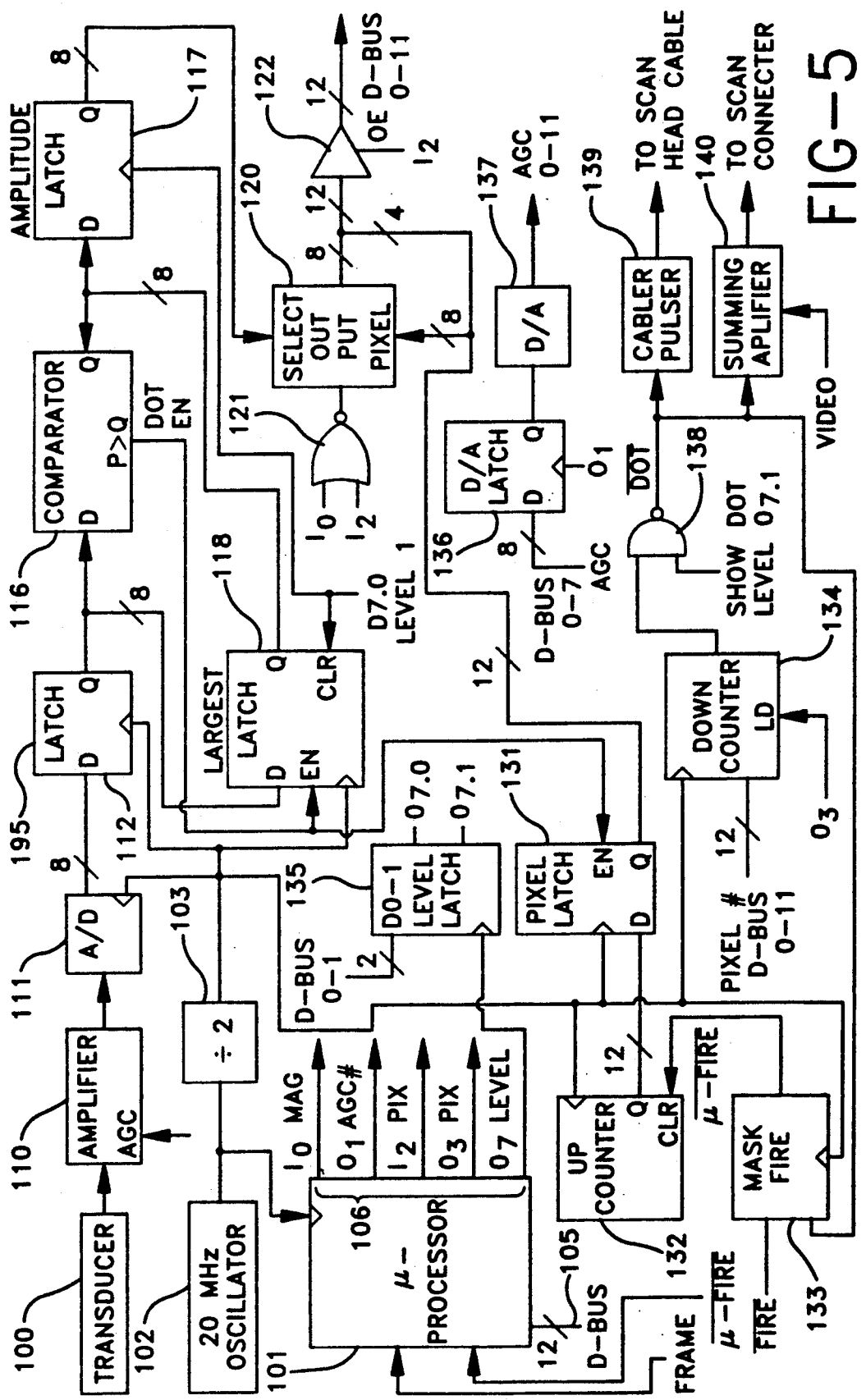
FIG. 5 is a detailed block diagram of an alternate approach for locating a transducer according to this invention.

Referring to FIG. 5 there is shown an ultrasonic position indicating apparatus which employs a microprocessor 101. As will be explained, the microprocessor 101 controls the operation of the circuitry to be described. The circuitry enables response to signals which occur during each of the scan lines and to locate a number of consecutive signals above a predetermined amplitude within a frame. By determining these consecutive signals one locates the position of the transducer in regard to the display. This enables one to show the transducer on the display by various means, such as a bright dot, an arrow, or any other way of highlighting the transducer with respect to the ultrasonic image display.

As one can see from FIG. 5, the microprocessor 101 receives the FRAME signal and the FIRE signal at the real time inputs. The microprocessor has a data bus 105 which, as will be explained, operates to interface with the above-noted circuitry. The microprocessor also has real time outputs designated generally by reference numeral 106 which enables control of the above-described circuitry. There is a 20 Mhz oscillator 102 which operates as a system clock. The output of the oscillator 102 is directed to the clock input of the microprocessor 101. The output of the oscillator 102 is also divided by two via a divider module 103 which output serves as the clock input to various other modules included in the system. Also shown in FIG. 5 is the transducer 100 which is positioned on a catheter which is directed into the body of a patient. It is of course understood that the transducer 100 can be located on any medical device. The transducer 100 is of the type which will emit or return a signal when ultrasonic waves impinge upon the surface of the transducer. The transducer provides this signal electrically as being a piezoelectric device or by other means. The output from the transducer is applied to the input of an amplifier 110 which amplifier is capable of having its gain controlled via the AGC input. The output of the amplifier is again applied to an analog-to-digital converter 111. The operation of the analog-to-digital converter is to convert the analog signals received from the transducer 100 at the input to digital signals at the output. The output from the analog-to-digital converter is directed to a latch 195. The function of the latch 195 is to store in real time each digital output or each 8 bit output of the analog-to-digital converter 111. The output of the latch 195 is directed to a comparator 116 and also to a second latch 118 The function of the second latch 118 is to store any signal which is larger than the previous signal from the analog-to-digital converter 111. Essentially the comparator 116 operates as the comparators described above. The comparator 116 takes the output from latch 115 and compares the output of latch 115 with the last largest signal stored in latch 118. If the signal from latch 115 is larger than the signal stored in latch 118, then the comparator causes the new larger signal to be stored in latch 118 for further comparison. The output of latch 118 is transferred to latch 117 under control of the microprocessor 101. In this manner latch 117 always has the largest signal stored therein. The output of latch 117 is directed to one input of a select output module 120. Module 120 as will be explained, essentially is a switch which is under the control of gate 121. The inputs to the gate 121 are obtained from the microprocessor outputs 106 which enables the select output switch to either select the largest amplitude signal as stored in latch 117 or to select the pixel signal which is stored in latch 131 as will be explained. The output of the select output module 120 is directed to an amplifier 122 which amplifier is coupled directly to the data bus 105 of the microprocessor.

Thus from the above, it is seen that the amplitude of the largest signal for each FIRE signal or ray which emanates from the transducer 100 is stored in latch 117. As indicated, a fire pulse is divided into a number of line segments to enable the pulse which is of largest magnitude to be defined in terms of an XY coordinate. In this manner when a large amplitude pulse appears and is stored in latch 115 one desires to know the fire pulse at which this pulse appeared as well as the position of the pulse between fire pulses. In this manner as explained above, the XY location of each pulse can be ascertained. In order to do this, the system includes an up-counter 132. The up-counter 132 receives the clock from the output of the frequency divider 103. Essentially the up-counter 132 is cleared during each fire pulse. As seen in FIG. 5 the fire pulse is also coupled to a masked fire circuit 133 which essentially is a one-shot. The masked fire circuit 133 resets the up-counter 132 at each fire pulse. The up-counter 132 begins to count up at the rate of one-half the clock frequency. In this manner each fire pulse is divided into a series of smaller intervals or segments by means of the up-counter. Each time the comparator 116 indicates that it has received a larger signal from the analog-to-digital converter, the pix latch 131 is also enabled. When the pix latch 131 is enabled the pixel or line segment at which the larger pulse appeared is automatically stored in latch 131. The output of latch 131 is directed to the other switching input of the select output module 120. In this manner the select output module 120 can either direct the pixel or the maximum amplitude to the output amplifier 122. There is also shown a down-counter 134 which also is clocked by means of the output of the divider 133. The down-counter is loaded by the microprocessor basically from the D bus 105 and receives the load signal from the microprocessor at the output designated as $O_8$ (PIX). The function of the down-counter 134 is as follows. When the microprocessor receives the largest amplitude signal during the fire pulse, it also receives the pixel number. In order to display the signal on the imaging system display, one must realize that when the ultrasonic wave hits the transducer surface 100 it is now being reflected back to the scanning head of the ultrasonic system. In this manner the propagation time is twice the time for the ultrasonic system. What is meant is that the transducer produces a pulse when the ray strikes the surface of the transducer. However, this pulse is reflected back through relatively the same path. Hence the time for the pulse to arrive at the ultrasonic system or the ultrasonic scanning head is twice the time it takes for the pulse to arrive at the transducer surface. In this manner the microprocessor loads the down-counter with twice the pixel number associated with that ray so that the down-counter 134 when it reaches the count of zero will be at the right place in regard to the picture format. The output of the down-counter is directed to gate 138 which is an AND gate. The other input to AND gate 138 is derived from the level changer 135 which is also controlled by the microprocessor 106. In this manner the microprocessor 106 activates the level changer 135 at suitable intervals and when the down-counter reaches zero, a dot is produced at the proper XY location on the display. This dot or pulse serves to highlight the display at the XY coordinate of the location of the transducer. The output of the dot gate 138 goes through a cable pulser 139 which, as indicated, can inject the pulse directly into the scanning head by means of electromagnetic coupling. The dot output can go directly to a summing amplifier 140 which again sums the video signal with the signal obtained from the ultrasonic imaging system and with the output of the summer directed to the scan converter as previously explained in regard to the circuit shown in FIG. 3. Thus one can ascertain briefly above how the circuitry works. In FIG. 5 there is also shown a digital-to-analog latch 136. The latch 136 has an input coupled to the bus 105 which comes from the microprocessor and has an output coupled to a digital-to-analog converter 137. The output of the digital-to-analog converter 137 is designated as AGC. As will be explained, the microprocessor provides a digital code which is converted to an analog signal to provide the AGC signal for amplifier 110. In this manner the signal provided by the microprocessor, as will be explained, is coupled to the input of the D/A latch 136 which essentially transfers this signal to the digital-to-analog converter 137. The digital-to-analog converter 137 converts the digital signal into an analog AGC signal which is applied to the AGC input of amplifier 110. In this manner a suitable AGC signal is provided to enable amplifier 110 to efficiently respond to any pulse received from the transducer 100.

Reference will now be had to FIGS. 6-12. It is noted that in regard to the discussion of these figures, there may be reference back to FIG. 5 to essentially show how the microprocessor 101 operates in conjunction with the remaining system components.

FIG. 6 shows a series of fire pulses which produces a frame. An ultrasonic system may employ 256 fire pulses to thereby produce a 256 line display or may produce 512 fire pulses to provide a display of 512 lines. The number of fire pulses employed in various ultrasonic systems can vary. Essentially each time a fire pulse is emitted, the ultrasonic system produces an ultrasonic beam of energy also designated as a ray.

The microprocessor serves to interrogate gate 121 (FIG. 5) to thereby cause the select output 120 to transfer to the microprocessor via amplifier 122 the maximum amplitude received during each fire pulse or ray and the pixel number or the location of that maximum pulse with respect to the ray. This is done by the microprocessor by activating inputs I$\phi$ and I-2 of gate 121. In this manner as shown in FIG. 7 the microprocessor has stored in a memory array the maximum amplitude and pixel number for each ray as O to N. The microprocessor as seen in FIG. 6 produces the pulses to operate gate 121 at the read time which is shown at a time right before the next fire pulse (dashed line). It is understood that the microprocessor is responsive to the fire pulse based on the FIRE input to the microprocessor. The microprocessor also computes the start and end of a frame, typically by noticing an interim of cessation of fire pulses. The microprocessor thereby monitors each of the fire pulses and controls the circuit accordingly. Thus as shown in FIG. 7, the microprocessor has stored in various memory locations the amplitude of the maximum pulse which occurs during each ray and the pixel or line segment at which the pulse occurs. At the end of a frame which constitutes N rays or N fire pulses as, for example, 256 or 512 or any other number, the microprocessor then adds all the amplitudes stored in the memory array for the given number of rays and divides the sum by the given number of rays. Thus for example, the microprocessor will add all the amplitudes stored in each of the memory locations designated as O to N and then divides the number by N+1. In this way the microprocessor obtains an average amplitude signal value for each frame. The average value for each frame is then subtracted from each amplitude value stored. In this way the microprocessor can suppress noise that may affect the pulses received during a frame. By responding to consecutive pulses of larger amplitudes the microprocessor can select the XY locations of the transducer. This will be explained in greater detail.

In FIG. 8A there is shown an enlarged view of the transducer 13 with a series of ultrasonic waves impinging on the surface and being reflected. FIG. 8B essentially shows the response of the transducer 13. It is seen, for example, that the amplitude at ray 6 as shown in FIG. 8B is larger with it being less at ray 5 and ray 7 and less at ray 4 and ray 8. In FIG. 7, it is shown that the same sequence of events occurs whereas the amplitude is maximum, namely 38 at ray 6, 33 at ray 5, 34 at ray 7, 35 at ray 8, and 30 at ray 4. Thus instead of searching for the largest magnitude pulse during the frame as previously described, the present system looks at groups of pulses to determine from such information where the transducer is. This further reduces any chance of random noise affecting the system, as random noise would not occur as a sequence of pulses. Furthermore, the system then develops an average voltage based on all the amplitudes stored during a frame to thereby control the threshold of the system according to the value stored. In order to fully understand the operation of FIG. 5 in conjunction with the explanation of the waveforms and storage array discussed in FIGS. 6, 7, and 8, reference is now made to the flow charts starting in FIG. 9.

Figure 9:
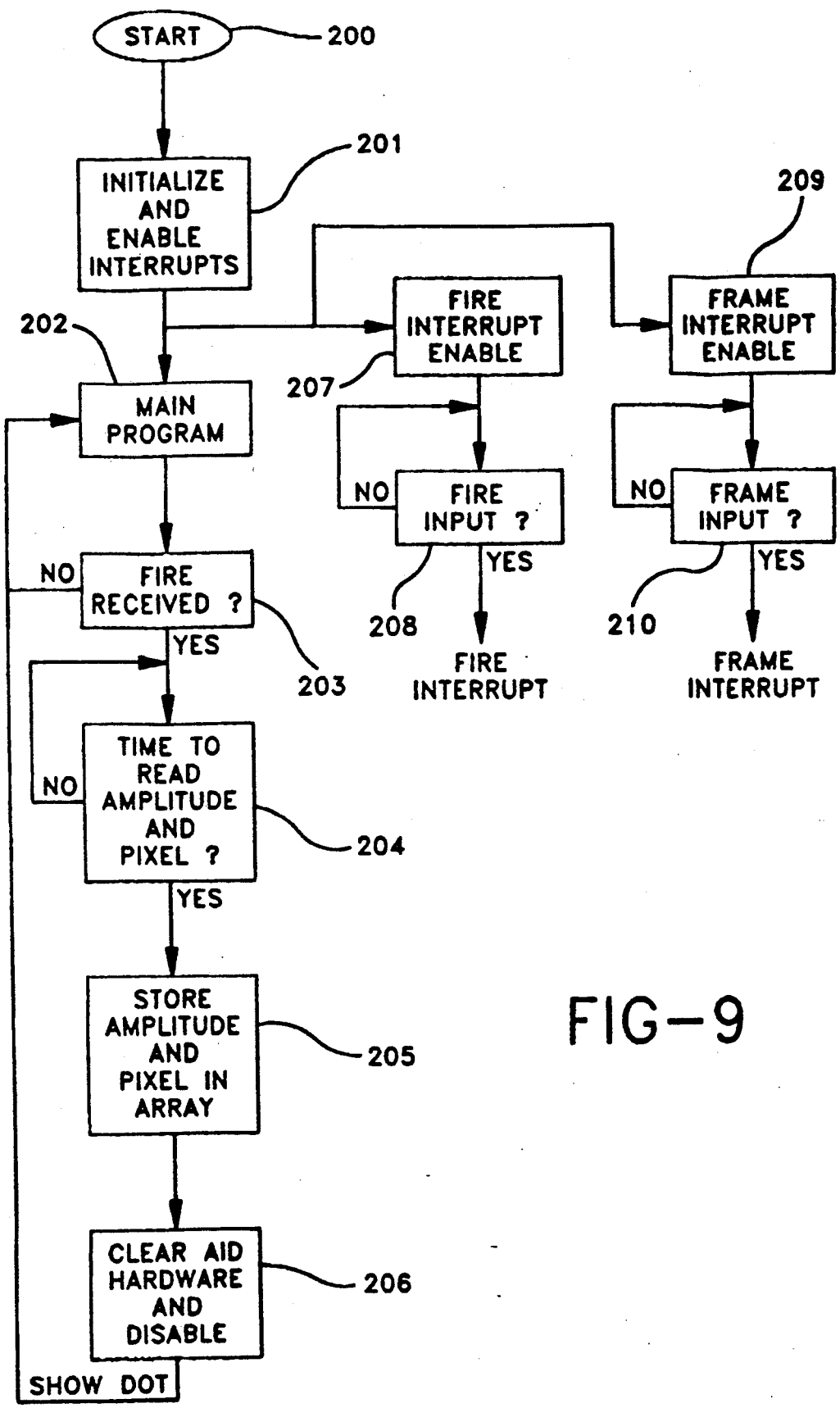
FIG. 9 is a flow chart depicting the sequence of operation performed by this system.

Thus referring to FIG. 9 there is shown a flow chart which is useful in explaining the operation of the microprocessor 101 of FIG. 5 and to further show operation of the system. The program starts at module 200 and 201 whereby there is an initialize and enable interrupts by the microprocessor. This enables the microprocessor 101 to be receptive to any information which appears on input lines designated as FRAME and FIRE. The microprocessor then begins to operate according to main program 202. This can be any type of program. The microprocessor 101 can be time shared or could perform operations according to the main program, for example, calculating the average of all values stored in the array as shown in FIG. 7 or compute the time between fire pulses, and so on as will be further explained. Essentially the microprocessor looks for a fire pulse to be received on its input line as shown in FIG. 5. Hence module 203 questions, Has a fire pulse been received? If a fire pulse has not been received then operation continues via the main program. If a fire pulse has been received, then the program questions whether it is time to read the amplitude and pixel number of the maximum transducer signal during the last fire period. This is done in module 204. Referring to FIG. 5, the microprocessor 101 receives the fire pulse and begins to count up from the receipt of the fire pulse as the microprocessor knows when to expect the next fire pulse. This is based on the repetition rate of the system. Therefore the microprocessor will initiate the read signal as shown in FIG. 6 before the next fire pulse is expected. This is a time calculation which is done by the microprocessor whereby the microprocessor at a given time indicates that it is time to read the amplitude and pixel as shown in module 204. The microprocessor then first activates the I$\phi$MAG output which causes gate 121 to select the output from amplitude latch 117 which then is applied via the amplifier 122 to the bus 105 of the microprocessor. Hence during this mode the microprocessor receives the amplitude of the signal. The microprocessor also knows which fire pulse this is as it receives all fire pulses and counts fire pulses. Hence the microprocessor already knows that this is the first fire pulse of the new frame or the second or the third and hence stores the amplitude in the memory array as shown in FIG. 7. The microprocessor then activates the I-2 PIX read which then causes switch 120 to select the pixel number from latch 131 and which again is directed to the output of amplifier 122 to give the microprocessor the pixel number. This is also stored in the memory array adjacent to the amplitude received. Thus as shown in module 205 the microprocessor stores the amplitude and pixel number in the array. After this is done the microprocessor as shown in module 206 clears the A/D converter hardware and disables show dot. This is done to prevent any ambiguities from occurring. The microprocessor then returns to the main program after the clear sequence as shown by module 206. Thus for each FIRE pulse the microprocessor "reads" the amplitude latch 117 and the pix latch 131 via the select output switch 120 and stores the maximum amplitude and pixel location in the memory array for each ray or FIRE pulse. As also seen in FIG. 9, after the initialization and enable interrupts in module 201 the microprocessor also executes a fire interrupt enable program each time a fire pulse appears. The microprocessor via module 207 looks for a fire pulse at the input. If there is a fire pulse the microprocessor enables the fire interrupt program. The microprocessor in module 208 interrogates to determine whether there is a fire pulse. If there is no fire pulse, the microprocessor returns to its initial status. If there is a fire pulse the microprocessor executes the fire interrupt program. In a similar manner as one can see, there is also a frame interrupt enable program as evidenced by module 209. Hence the microprocessor also looks for a frame signal on the other input lead. If there is a frame signal, the microprocessor institutes the frame interrupt program as evidenced by module 210. If there is not a frame signal, the microprocessor waits for another input from module 209.

Figure 10:
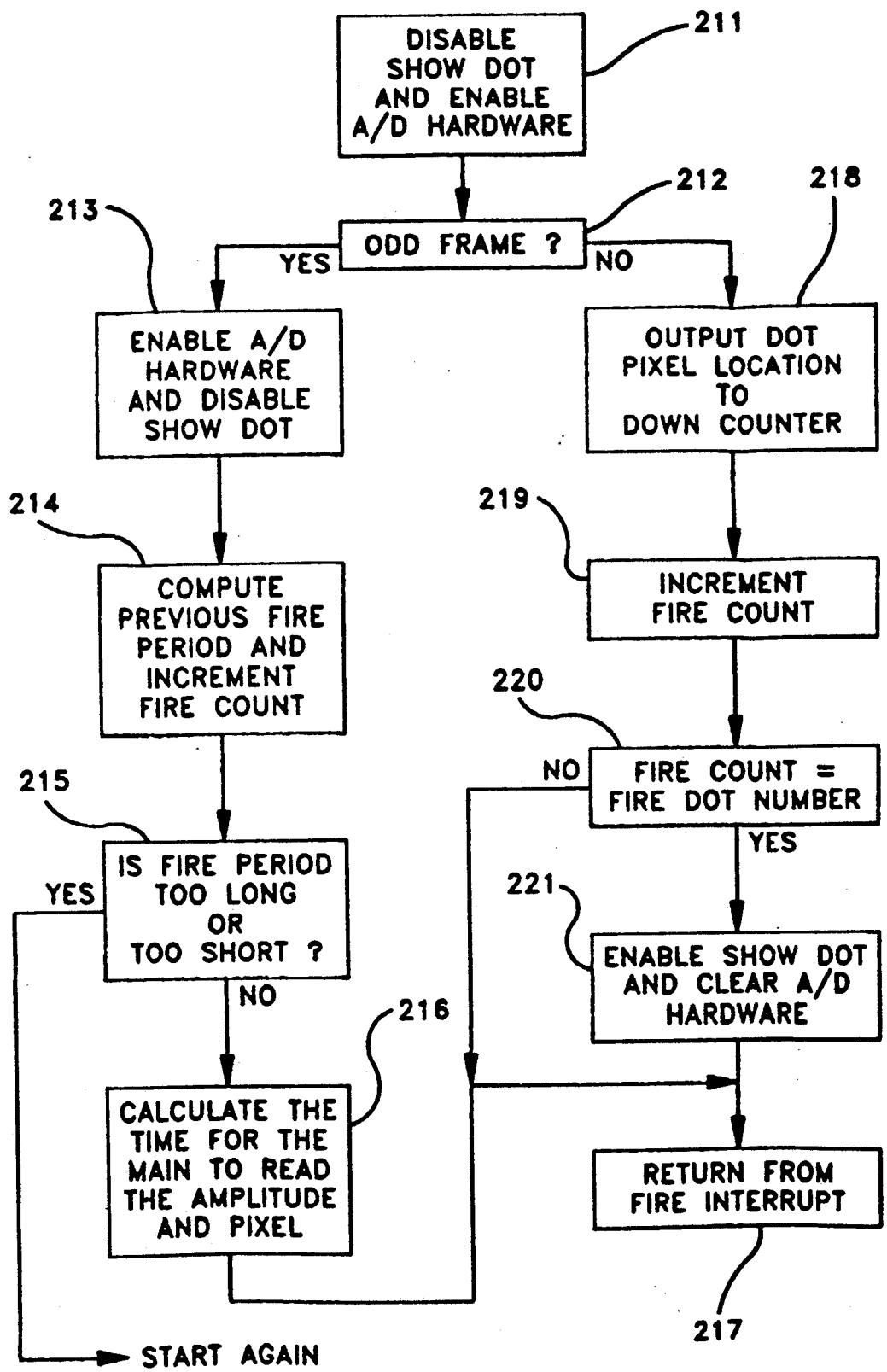
FIG. 10 is another flow chart useful in describing the fire interrupt mode implemented by this system.

Referring to FIG. 10 there is shown the flow chart for the fire interrupt mode as indicated by module 208 of FIG. 9. During the fire interrupt mode the microprocessor then disables the show dot and enables the analog-to-digital hardware as evidenced by module 211. Referring to FIG. 5 the microprocessor disables the show dot gate 138 by means of the level changer latch 135 which is set by the microprocessor during the fire interrupt mode and during the fire pulse the microprocessor also enables latch 117 and clears the largest value latch 118 to allow the new fire pulse to commence operation. The system operates so that it collects data during all odd frames as 1, 3, 5, 7, and so on and transmits data during all even frames as 2, 4, 6, 8, and so on. This is just a convenient way of operation on a frame-to-frame basis and essentially any other combination of collecting and transmitting data based on various frames and so on can be implemented as well. Hence FIG. 10 shows a module 212 which indicates odd frame. If it is an odd frame, the system will collect data. Thus the output from module 212 designated as YES is directed to module 213 which specifies that the microprocessor enables the A/D converter 111 hardware and disables the show dot. This is redundant as this was done in module 211 but is a further check to assure reliable operation. Thus the same latches as 117 and 118 are set as well as the fact that the level changer and show dot gate 138 are disabled. Then the microprocessor proceeds to compute the previous fire period and to increment the fire count 214. As indicated, the microprocessor knows exactly the fire period which is the period between fire pulses and essentially counts down until it reaches a count indicative of the read location where the microprocessor will read the maximum amplitude and pixel values as described above. In the meantime the microprocessor computes the fire period and starts incrementing the fire count as evidenced by module 214. As shown in module 215 the microprocessor knows if the fire period is too long or too short. Essentially, the microprocessor will determine that it has received a fire pulse which is an improper pulse. If that occurs, then the microprocessor will determine that the fire period is too short or too long if the fire pulse does not appear when anticipated as evidenced by module 215. If either event occurs, the microprocessor is instructed to start over again. As one can see this will not affect circuit operation. If a proper fire pulse is received, the microprocessor calculates the time for the system to then read the amplitude and pixel value via gate 121 as described, and this occurs in module 216. After that is done, the microprocessor is finished with that phase and there is a return from the fire interrupt sequence as determined by module 217. Again referring to FIG. 10, if the frame is not an odd frame and therefore is an even frame as evidenced by module 212, then data is transmitted. As seen via module 218, the microprocessor loads the down-counter 134 of FIG. 5 with the output dot pixel location as explained above. Thus the microprocessor enables down-counter 134 via the output leads. The microprocessor then, as evidenced by module 219, increments the fire count accordingly. As one can understand, the microprocessor receives the dot pixel location and stores it via the array. The microprocessor knows what pixel or the Y location that the maximum amplitude pulse occurred at. The microprocessor also knows the ray or the fire pulse at which this maximum amplitude occurred. Therefore the microprocessor increments the fire counter 219. When the fire count equals the fire dot number which essentially says that the pixel is now at the correct ray or line, the microprocessor then enables the down-counter 134 via the LD input to enable the down-counter to begin counting down during that fire pulse as explained above. The microprocessor will then also enable gate 138. In this manner when the down-counter reaches the count of zero, a pulse is produced at the output of gate 138 to thereby increase the intensity of the display. This clearly indicates the location of the transducer on the display either via the cable pulser 139 or via the summer amplifier 140. After this has been accomplished as shown by module 221 the system then goes into the return from fire interrupt mode 217 back to the main program or back to module 207.

Figure 11:
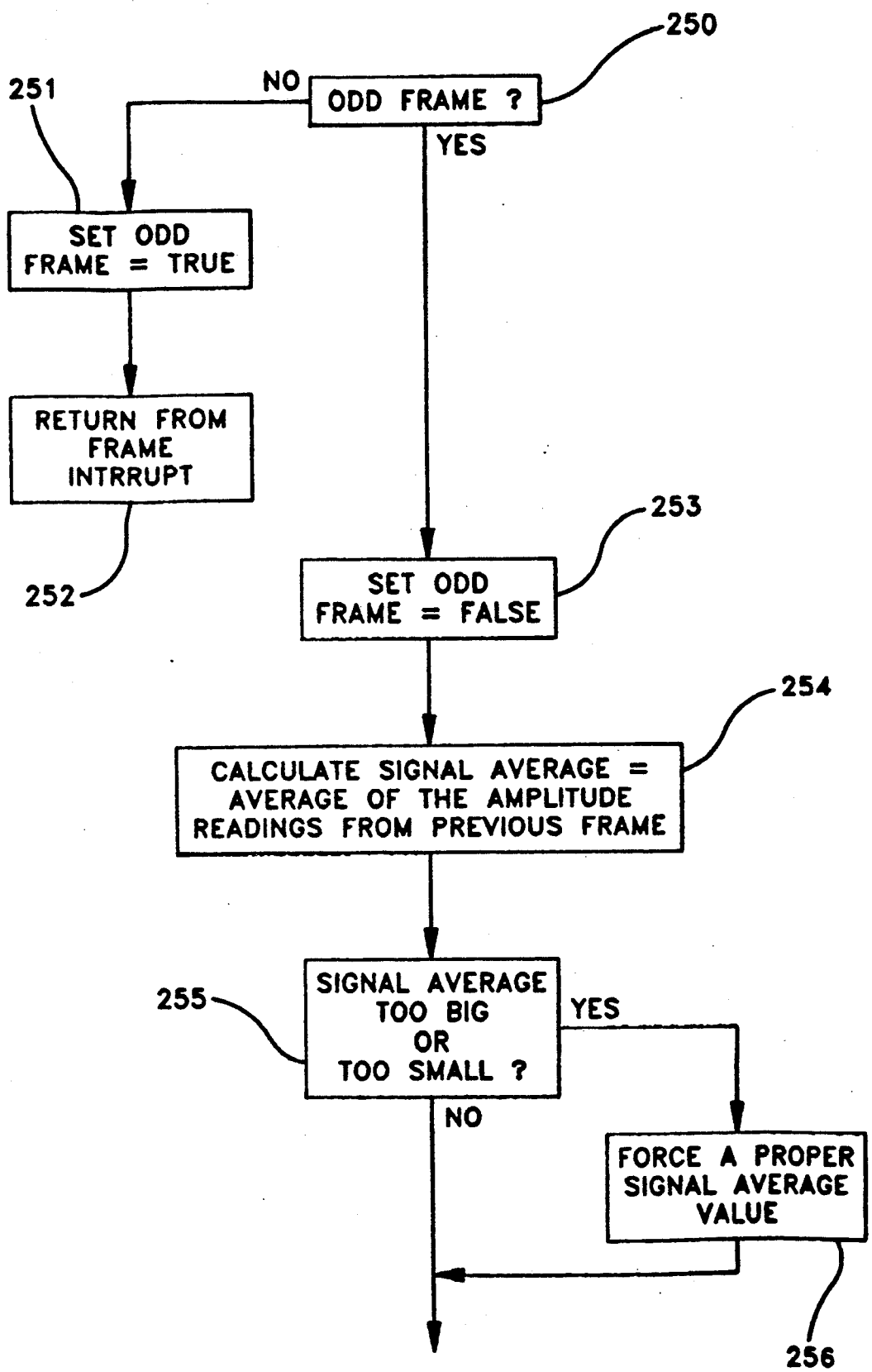
FIG. 11 is a flow chart useful in describing a frame interrupt mode.

Referring to FIG. 11 there is shown the frame interrupt sequence as, for example, further depicted in regard to FIG. 9. During the frame interrupt the microprocessor upon receiving a frame interrupt pulse at the input makes a determination as to whether this is an odd frame or an even frame. As indicated above, the data is collected during odd frames and transmitted during even frames but the particular sequence utilized is of no significance. This is done via module 250. If it is an odd frame, the microprocessor sets the odd frame indicator to FALSE as shown in module 253. What this means is that the next frame will be an even frame. After setting the odd frame indicator to FALSE, the microprocessor then produces the signal average as described above. In this manner the microprocessor then adds all of the amplitudes stored in the array for the frame and divides that value by the number of locations in the array to obtain the signal average. The microprocessor then determines via module 255 as to whether or not the signal average is too big or too small. This is done strictly on pre-program thresholds which are programmed into the microprocessor as will be clearly understood. If the signal average is too big or too small, the microprocessor forces an average signal value via module 256 to be used by the circuitry. Thus the microprocessor upon determination that the average signal value for that particular frame was too big or too small will set some sort of average value which is indicative of a noise level. If the signal average is not too big or too small, then the microprocessor indicates this via the no input and continues the frame interrupt processing which will be described in conjunction with FIG. 12.

Referring to FIG. 12 there is shown the operation of the microprocessor in selecting groups of pulses in order to determine whether a transducer signal has been received. Thus as seen in FIG. 12, the microprocessor after providing the contents of the array as, for example, shown in FIG. 7, now proceeds to scan the array to find groups of five or more consecutive returns or consecutive fires whose pixel numbers are within ten of each other. Essentially what the microprocessor will do is to look at all the pixel values and the amplitudes to determine whether or not there has been sufficient amplitude in consecutive fires at consecutive rays where the pixel numbers are essentially the same as, for example, shown for rays 4–8 with pixel numbers 22, 23, 24, 25, and 28. If this occurs then next thing the microprocessor does is to determine whether this group of pulses has an amplitude larger than any other consecutive groups found and which is above the signal average. Essentially as indicated in module 258, what the microprocessor does is to look at all values in the array and to determine whether there are any five other consecutive pulses having larger amplitudes and with consecutive pixel numbers. If the microprocessor does find such a group, the microprocessor will find the fire number which is the ray of the largest amplitude in the group and save this in the fire dot number as indicated in module 258. The microprocessor must find a consecutive group whose amplitude is larger than any other group found and above the signal average. As previously indicated, the microprocessor computes the signal average by adding the total value of each pixel amplitude in each of the array locations and divides by the number of memory locations in the array. This then constitutes the signal average for an entire frame. Again referring to FIG. 7, assume that after computing a signal average for the entire frame that the microprocessor computes the signal average to be 10. The microprocessor then subtracts the value of 10 from each location as, for example, from locations 0, 1, 2--N. As seen, the amplitude in ray location 1 is 9 at pixel 27. If the average signal level was 10, then this signal which is less than 10 is ignored. The value at ray location 2 would also be zero and hence be ignored and the value at ray 3 would be ignored. The value at ray 4 which is 30 would be reduced to 20. The value at 5 which is 33 would be reduced to 23, and so on. In this manner the system ignores all noise pulses in determining the location of the transducer and hence can average out and eliminate all signals which are not above the computed average amplitude. This is how the microprocessor finds the consecutive groups as indicated by module 258. If such a group is found, the microprocessor will then find the fire number of the largest amplitude in the group and save this in the fire dot number. Again referring to FIG. 7, this amplitude would be amplitude 38 for ray 6 which is the largest amplitude in the fire dot group number. In a similar manner the microprocessor will find the pixel number of the largest amplitude in the group number and save this in the dot pixel number as indicated by module 260. Again referring to FIG. 7 this will be pixel 24. The microprocessor then finds the value of the largest amplitude in the group and computes a new AGC number as indicated in module 261. Thus the largest value is 38 which, based on an average signal of 10, would be reduced to 28. Now the microprocessor is programmed with one of many, many available algorithms which essentially indicates that since the average signal was 28, it would be desired to look at a signal of twice that value. Therefore the AGC signal would now be controlled to allow the amplifier 110 of FIG. 5 to increase its gain to obtain twice the amplitude output signal. Thus this AGC number is outputted and directed, for example, to the input of the latch 136 where it is converted to a analog value based on the digital-to-analog converter 137 and as shown in module 262 of FIG. 12 to control the gain of the amplifier accordingly. After this is done, one returns from the frame interrupt program as indicated by module 263. It is also shown returning to the frame interrupt program of FIG. 12 (module 257), if the microprocessor cannot find five groups of consecutive returns in a frame whose pixel numbers are within 10 of each other, then the system provides a new AGC number that gives the maximum amplifier gain as shown in module 264. Hence if during a frame there are no consecutive pixels the microprocessor produces an output number which is stored in latch 136 which output number will be converted to an analog signal by the digital-to-analog converter 137 to operate the amplifier 110 at maximum gain. The system then makes the fire dot number non-displayable as evidenced by module 265. In this particular instance the microprocessor indicates that a transducer location could not be found during an entire frame and therefore there is no reason to operate the down-counter 134 or the dot gate 138 and therefore the dot becomes non-displayable as indicated by module 266. As one can understand, the system of FIG. 5 is constantly selecting the largest magnitude signal including the pixel number of this signal found during each line or each ray. After all these signal amplitudes are added up and averaged out, the average signal is subtracted. If the remainder does not exceed a predetermined value, there is no signal in that frame which is indicative of the presence of a transducer. This is quite possible during an ultrasonic examination by a practitioner. If this exists, then the system will operate at maximum gain until a transducer signal is found. Similarly requiring that a sequence of pulses be detected serves to ensure reliable operation. It is indicated that the above technique for producing an average signal to be subtracted from all outputs found during each ray is extremely important as it serves to substantially reduce noise and provide for reliable operation.

We claim:

1. An apparatus for responding to a first transducer within an area of a body, said first transducer of the type which responds to ultrasonic energy impinging on a surface thereof emitted by a second transducer, comprising:

an ultrasound imagining system for imaging an area of the body to cause said first transducer to provide return signals each time ultrasonic energy from said second transducer impinges thereon, said system including first means for providing a display of said area by converting imaging information into a given number of scan lines to cover said area with said given number of scan lines indicative of a frame, second means response to said return signals during said frame to analyze the amplitudes of said return signals on a frame to frame basis, said second means providing a control signal in each frame for controlling the analysis by said second means of the next succeeding frame.

2. The apparatus according to claim 1, wherein said means responsive to said return signals includes means for dividing each scan line into a plurality of segments,
   means for indicating the segment of each line where a return signal is present to provide a pixel number for each line having a returned signal.

3. The apparatus according to claim 2, further including means responsive to each of said return signals for providing and storing a representation of the amplitude of said return signals for each line during a frame.

4. The apparatus according to claim 3, including means responsive to each said representation stored to obtain an average of the amplitude of said return signals over a frame, and
   means responsive to said average for reducing said representation as stored for each line.

5. The apparatus according to claim 4, further comprising:
   selection means responsive to the reduced said representation stored for each line for selecting the largest stored amplitude for a given number of consecutive lines in a frame having pixel numbers which are less than a selected number from one another, and
   means responsive to said selection means to provide a line number and a segment number for the consecutive lines indicative of the position said first transducer.

6. The apparatus according to claim 5, including means responsive to said line number and segment number to indicate the position of said transducer on said display.

7. An apparatus for locating the position of a first transducer within an area of a body, said first transducer of the type which responds to ultrasonic energy impinging on a surface thereof emitted by a second transducer, comprising:

an ultrasound imaging system for imaging the area of the body to cause said first transducer to provide return signals each time ultrasonic energy from said second transducer impinges thereon, said imaging system including means for providing a display of said area of said body by providing a given number of scan lines to cover said area with said given number of scan lines comprising a frame, and means responsive to said return signals to analyze said return signals corresponding to each scan line within said frame to determine which ones of said return signals are of the highest amplitude and are indicative of the location of said first transducer and to provide coordinate locations for said first transducer location.

8. The apparatus according to claim 7, wherein said means for providing a display of said area includes a scan controller to image said area with a given number of scan lines per frame, with a given number of frames per second, said scan controller providing a frame start signal and a frame stop signal, with a plurality of FIRE signals located therebetween with each FIRE signal corresponding to one of said scan lines.

9. The apparatus according to claim 8, wherein said means responsive to said return signals includes,
   line counting means operative to provide a line number during the presence of one of said return signals indicative of a first coordinate,
   pixel generating means operative to divide each line into a plurality of segments, means responsive to the presence of said return signals indicative of a first coordinate to provide a pixel number indicative of a second coordinate, whereby said first and second coordinates define said first transducer location during said frame.

10. The apparatus according to claim 7, wherein said transducer is positioned on and secured to a catheter adapted to be located in said body tissue.

11. A method of locating the position of a first transducer present in a body, said first transducer of the type emitting a signal when ultrasonic energy from a second transducer impinges thereon, comprising the steps of:
detecting said signal emitted during a frame, and
defining the location of said signal in terms of a line contained within said frame and a position on said line to thereby define the location of said first transducer during said frame.

12. The method according to claim 11, wherein each line in said frame is indicative of the transmission of an ultrasonic pulse.

13. The method according to claim 11, wherein the step of defining said location includes the steps of dividing said line into a plurality of pixels and defining the pixel as said position on said line during a scan of said area.

14. Apparatus for locating the position of an object within a body, comprising:
first transducer means located on said object and capable of emitting a signal when ultrasonic signals emitted from a second transducer means impinges thereon,
an ultrasound imaging system for providing an imaged area of said body, said imaging system including means for scanning said image area nd to present a scanned area in terms of a plurality of scan lines with said plurality of scan lines indicative of a frame,
means coupled to said first transducer means for measuring a predetermined signal characteristic from the signals emitted by said second transducer means during a frame, and
means responsive to signals emitted by said first transducer to provide an X and Y coordinate for a maximum measured value of said signal characteristic within said scanned area of each frame.

15. The apparatus according to claim 14, further comprising;
display means included in said imaging system for displaying the contents of said scanned area during each frame, and
means responsive to said X and Y coordinates for inserting a marker indication on the display for each frame indicative of the location of said maximum measured value and therefore said first transducer.

16. The apparatus according to claim 15, further including means responsive to said first transducer signal to compare the same with a threshold, wherein if any of said first transducer signal said threshold a control signal is provided and means responsive to said control signal for storing the value of said first transducer signal as exceeding said threshold.

17. In an ultrasound imaging system operative to image an area of a patient's body with ultrasonic pulses, said imaging system including scan controller means for providing a given number of lines during a frame, with each line indicative of the information received by said system during an associated pulse, the combination therewith of apparatus for locating the position of an object within said area of said patient's body comprising:
transducer means located on said object and operative to produce and emitted signal when ultrasonic energy impinges thereon,
first means coupled to said transducer means and responsive to said emitted signal to provide an output signal according to said emitted signal,
second means for comparing said output signal with other emitted signals to detect larger amplitude emitted signals during a line, and
third means responsive to said detection of said larger amplitude emitted signals during each line for providing an X and Y coordinate indicative of said larger amplitude emitted signals for each line in a frame,
fourth means responsive to said larger amplitude emitted signals and said X and Y coordinate to store said larger amplitude emitted signals during said frame, and
means responsive to the stored signals for selecting those signals indicative of the location of said transducer during said frame.

18. The apparatus according to claim 17, wherein said first means includes amplifier means for amplifying said emitted signal at an output terminal,
an analog to digital converter having an input coupled to said output terminal for providing a digital signal at an output of a value indicative of the amplitude of said emitted signal.

19. The apparatus according to claim 18, wherein said second means includes a first comparator having an input coupled to a noise level digital number and a second input coupled to the output of said analog to digital converter to provide an output signal when said second input exceeds said first input, and latch means responsive to said output signal for storing the value of said emitted signal.

20. The apparatus according to claim 19, wherein said third means includes a second comparator having one input coupled to said transducer and another input coupled to the output of said analog to digital converter for comparing said emitted signal stored within said latch means with new emitted signals from said analog to digital converter, and for providing an output signal when said new emitted signal exceeds said emitted signal stored within said latch means and means for causing said latch means to store said new emitted signal whereby said latch means will have stored therein the largest emitted signal produced within said frame.

21. The apparatus according to claim 20, wherein said fourth means includes:
first counting means for counting each scan line during a frame and means coupled to said counting means for storing said counted line during the detection of said largest emitted signal, and indicative of said X coordinate, and
second means operative to divide each of said lines into segments and including means for storing said segments and including means for storing said segment during the detection of said largest emitted signal indicative of a Y coordinate.

22. The apparatus according to claim 19, further including a digital to analog converter having an input coupled to the output of said latch means for providing an analog signal at an output terminal, with said output terminal coupled to said amplifying means for controlling the gain thereof according to the value of said emitted signal stored within said latch means.

23. The apparatus according to claim 17, further including video display means coupled to said scan converter means for providing a video display of each frame, and marker means coupled to said fourth means for highlighting said X-Y coordinate location on said display to distinguish the location of said object from the remainder of said display.

24. The apparatus according to claim 23, wherein said marker means includes means for causing said X and Y coordinate location to blink.

25. The apparatus according to claim 23, wherein said marker means includes means for providing a color indication at said X and Y coordinate location.

26. The apparatus according to claim 17, further including means for comparing the X coordinates for the previous frame with the present frame and providing an output when they are equal, means responsive to said output for inserting a signal into said imaging signal to mark the location of said transducer.

27. Apparatus for responding to a transducer located within an area of interest, said transducer of the type which responds to ultrasonic energy impinging thereon by producing return signals, comprising:
an ultrasonic imaging system of the type for imaging said area by providing a series of ultrasonic rays transmitted to said area for responding to reflected signals from said area, said system including display means for providing a display of said area with at least each one of said rays indicative of one scan line of said display with a given number of scan lines constituting a frame, whereby said transducer returns said return signals from said rays which impinge thereon at said transducer location within said area,
means responsive to said return signals for providing the maximum value of the returned signals during each ray for each frame and for storing the maximum values achieved for each ray,
means responsive to said stored signals for deriving an average value of said return signals stored for each frame, and
means responsive to said average value for providing the coordinate locations of said return signals stored during a frame.

28. The apparatus according to claim 27, further including:
means responsive to said series of rays to divide each ray into a plurality of segments to provide together with the location of each ray, a segment indication at the location indicative of the X, Y location of said return signals on said display.

29. The apparatus according to claim 28, further including:
means responsive to the locations of each ray of signals returned to said transducer for displaying the locations on said display.

30. The apparatus according to claim 27, wherein said means responsive to the locations of each ray provides the magnitude and segment location of the maximum value returned signal for each ray.

* * * * *